US012708444B2

(12) United States Patent
Richard

(10) Patent No.: US 12,708,444 B2
(45) Date of Patent: Aug. 18, 2026

(54) COMPUTER-ASSISTED SHOULDER SURGERY AND METHOD

(71) Applicant: ORTHOSOFT ULC, Montreal (CA)

(72) Inventor: Alain Richard, Lachine (CA)

(73) Assignee: ORTHOSOFT ULC, Montreal (CA)

( * ) Notice: Subject to any disclaimer, the term of this patent is extended or adjusted under 35 U.S.C. 154(b) by 268 days.

(21) Appl. No.: 18/346,822

(22) Filed: Jul. 4, 2023

(65) Prior Publication Data

US 2024/0008926 A1 Jan. 11, 2024

Related U.S. Application Data

(60) Provisional application No. 63/359,378, filed on Jul. 8, 2022.

(51) Int. Cl.

| | |
|---|---|
| ***A61B 34/10*** | (2016.01) |
| ***A61B 8/00*** | (2006.01) |
| ***A61B 8/08*** | (2006.01) |
| ***G16H 20/40*** | (2018.01) |

(52) U.S. Cl.

CPC .............. *A61B 34/10* (2016.02); *A61B 8/085* (2013.01); *A61B 8/4227* (2013.01); *A61B 8/4455* (2013.01); *A61B 8/4477* (2013.01); *G16H 20/40* (2018.01); *A61B 2034/105* (2016.02)

(58) Field of Classification Search

None

See application file for complete search history.

(56) References Cited

U.S. PATENT DOCUMENTS

| | | | |
|---|---|---|---|
| 8,007,448 B2 | 8/2011 | Moctezuma de La Barrera | |
| 2005/0020918 A1* | 1/2005 | Wilk | A61B 8/00 600/439 |
| 2017/0007330 A1* | 1/2017 | Britton | A61B 34/10 |
| 2017/0100092 A1* | 4/2017 | Kruse | G01S 7/5202 |
| 2021/0290313 A1 | 9/2021 | Cerda-Carvajal et al. | |
| 2021/0322148 A1 | 10/2021 | Mitra et al. | |
| 2022/0039868 A1* | 2/2022 | Chaoui | A61B 34/25 |

FOREIGN PATENT DOCUMENTS

| | | |
|---|---|---|
| CN | 112 155 733 B | 1/2022 |

* cited by examiner

*Primary Examiner* — Keith M Raymond
*Assistant Examiner* — Ashish S. Jasani
(74) *Attorney, Agent, or Firm* — NORTON ROSE FULBRIGHT CANADA LLP

(57) ABSTRACT

A system for computer-assisted guidance in glenohumeral joint surgery may have a processor unit, and a non-transitory computer-readable memory communicatively coupled to the processor and comprising computer-readable program instructions executable by the processor unit for: obtaining a natural range of motion profile for the glenohumeral joint by tracking movement of a humerus relative to a scapula of the glenohumeral joint in a non-invasive natural state, registering intra-operatively the humerus and the scapula to a referential system, fitting the natural range of motion profile to the humerus and the scapula in the referential system, creating an intraoperative range of motion profile for the glenohumeral joint by tracking movement of the humerus relative to the scapula of the glenohumeral joint intraoperatively, and outputting the intraoperative range of motion for the glenohumeral joint as a function of the natural range of motion.

20 Claims, 5 Drawing Sheets

ULTRADOUND IMAGING DEVICE
COORDINATE TRACKING DEVICE
Db
Da
D
R
Ob
Oa
O
1
2
4
6
6a
6b
8
8a
8b 10
14
H
12
16
14
S
14

2
50
PROCESSOR
52
I/O INTERFACE
51
MEMORY
INSTRUCTIONS
53

COMPUTER-ASSISTED SHOULDER SURGERY AND METHOD

CROSS-REFERENCE TO RELATED APPLICATION

The present application claims the benefit of U.S. Patent Application No. 63/359,378, filed on Jul. 8, 2022 and incorporated herein by reference.

TECHNICAL FIELD

The application relates generally to computer-assisted surgery systems of the type used in shoulder surgery involving the humerus and/or the scapula.

BACKGROUND OF THE ART

The glenohumeral joint is a known source of anatomical disorders or pathologies. As a result of such glenohumeral joint issues, humans can endure shoulder pain, can have limited range of motion. Accordingly, shoulder surgery is a common occurrence to resolve such patient conditions. However, the complexity of the glenohumeral joint, notably the anatomy of the glenoid and presence of various ligaments and layers of soft tissue, may present a challenge in performing shoulder surgery.

Computer-assisted surgery (CAS) systems have been devised to assist surgeons in effecting shoulder surgery, for instance by navigating the humerus and/or the glenoid. Nevertheless, there remains a need for improved surgical tools which may be used in conjunction with a CAS system in order to digitally navigate a humerus and/or position an implant on a glenoid in order to improve a patient's condition.

SUMMARY

In one aspect, there is provided a system for computer-assisted guidance in glenohumeral joint surgery comprising: a processor unit, and a non-transitory computer-readable memory communicatively coupled to the processor and comprising computer-readable program instructions executable by the processor unit for: obtaining a natural range of motion profile for the glenohumeral joint by tracking movement of a humerus relative to a scapula of the glenohumeral joint in a non-invasive natural state, registering intra-operatively the humerus and the scapula to a referential system, fitting the natural range of motion profile to the humerus and the scapula in the referential system, creating an intraoperative range of motion profile for the glenohumeral joint by tracking movement of the humerus relative to the scapula of the glenohumeral joint intraoperatively, and outputting the intraoperative range of motion for the glenohumeral joint as a function of the natural range of motion.

Still further in accordance with the aspect, for instance, obtaining the natural range of motion profile includes creating the natural range of motion profile for the glenohumeral joint.

Still further in accordance with the aspect, for instance, creating the natural range of motion profile for the glenohumeral joint includes tracking movement of the humerus relative to the scapula of the glenohumeral joint in the non-invasive natural state.

Still further in accordance with the aspect, for instance, tracking movement of the humerus relative to the scapula of the glenohumeral joint in the non-invasive natural state includes tracking the movement pre-operatively without disrupting a soft-tissue envelope covering the glenohumeral joint.

Still further in accordance with the aspect, for instance, tracking movement of the humerus relative to the scapula of the glenohumeral joint in the non-invasive natural state includes tracking the humerus and the scapula using at least one ultrasound imaging device.

Still further in accordance with the aspect, for instance, tracking the humerus and the scapula using at least one ultrasound imaging device includes tracking the scapula with a vest on soft-tissue covering the scapula, the vest including a plurality of ultrasound probe units.

Still further in accordance with the aspect, for instance, the system may include the vest with the plurality of ultrasound probe units.

Still further in accordance with the aspect, for instance, tracking movement of the scapula includes optically tracking the vest.

Still further in accordance with the aspect, for instance, tracking the humerus and the scapula using at least one ultrasound imaging device includes tracking the humerus with a wearable band on soft-tissue covering the humerus, the wearable band including a plurality of ultrasound probe units.

Still further in accordance with the aspect, for instance, the system may include the wearable band with the plurality of ultrasound probe units.

Still further in accordance with the aspect, for instance, tracking movement of the scapula includes optically tracking the wearable band.

Still further in accordance with the aspect, for instance, creating the natural range of motion profile for the glenohumeral joint includes creating the natural range of motion profile pre-operatively or peri-operatively, prior to soft-tissue incisions being made to access the glenohumeral joint.

Still further in accordance with the aspect, for instance, registering intra-operatively the humerus and the scapula to a referential system includes obtaining points on the humerus and on the scapula.

Still further in accordance with the aspect, for instance, registering intra-operatively the humerus and the scapula to a referential system includes merging virtual bone models to the points obtained on the humerus and on the scapula.

Still further in accordance with the aspect, for instance, merging virtual bone models includes obtaining patient-specific bone models.

Still further in accordance with the aspect, for instance, merging virtual bone models includes obtaining bone models from an atlas.

Still further in accordance with the aspect, for instance, the system may track the humerus and the scapula relative to the referential system continuously after the registering.

Still further in accordance with the aspect, for instance, tracking the humerus and the scapula includes tracking alterations to the humerus.

Still further in accordance with the aspect, for instance, tracking alterations to the humerus includes a retroversion angle and/or an inclination angle for a plane of resection.

Still further in accordance with the aspect, for instance, outputting the intraoperative range of motion includes outputting a gain or loss of range of motion relative to the natural range of motion.

DESCRIPTION OF THE DRAWINGS

Reference is now made to the accompanying figures in which.

DETAILED DESCRIPTION

Figure 1:
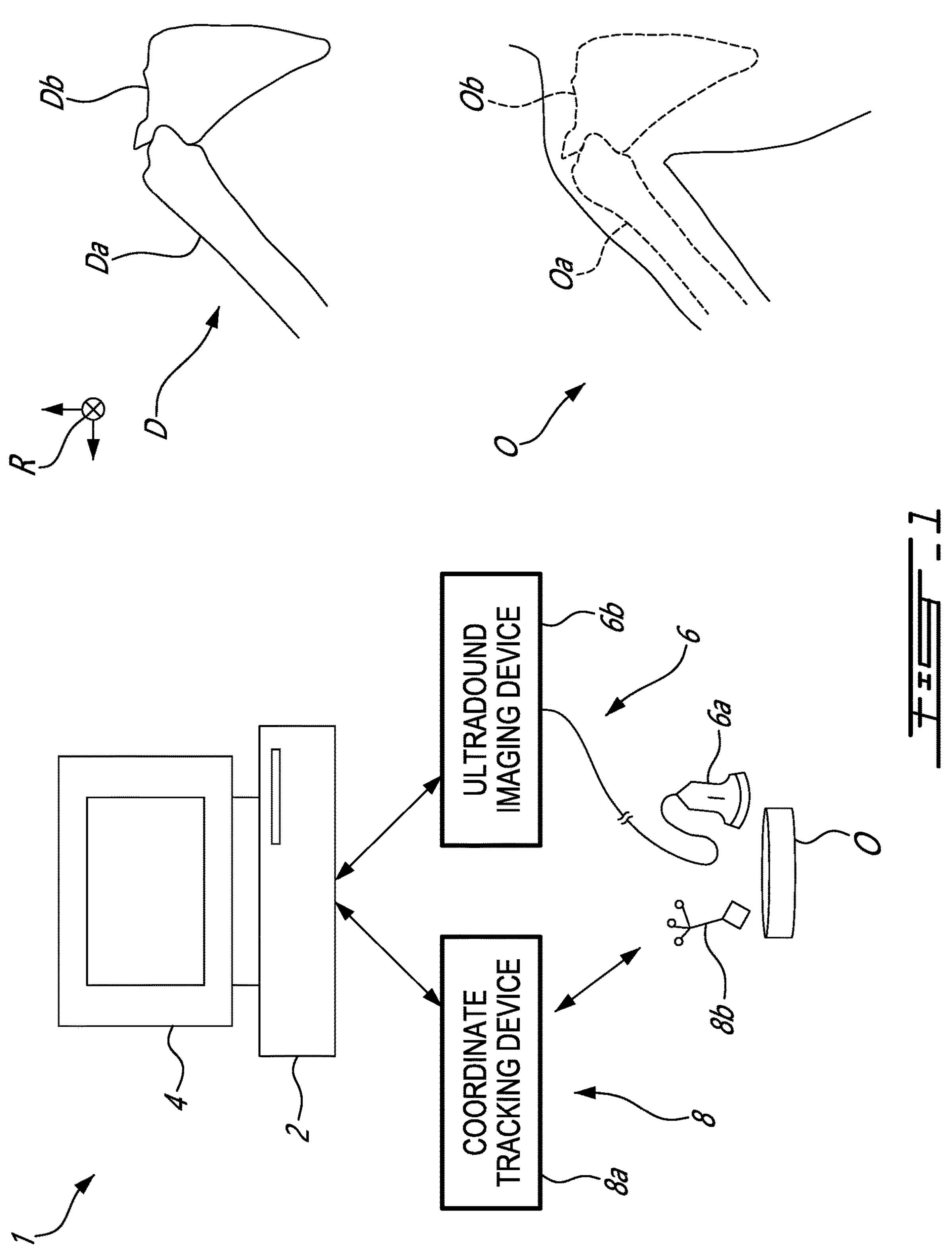
FIG. 1 is a schematic view of a system for computer-assisted guidance in glenohumeral joint surgery in accordance with a variant of the present disclosure.

Referring to the drawings and more particularly to FIG. 1, a system for computer-assisted guidance in glenohumeral joint surgery (a.k.a., shoulder joint, gleno-humeral joint) in accordance with the present disclosure is generally shown at 1. The system 1 is of the type that may be used to assist in altering the humeral head and/or the glenoid of the scapula. The glenohumeral joint surgery may be of different types, such as total shoulder arthroplasty, total reverse shoulder arthroplasty, partial shoulder arthroplasty, or other orthopedic shoulder surgeries that include alterations to the humerus and/or scapula, etc, and may even be used in some shoulder surgical procedures that attend to tissue in the shoulder (e.g., tendons, ligaments, cartilage, osteophytes). In an embodiment, the glenohumeral joint surgery includes cutting a plane on the humeral head, for instance in the context of glenoid surgery or reverse glenoid surgery. The system 1 may be used for different operations as well, including preserving the native humeral head, and adding an implant to the glenoid.

An embodiment of the system 1 is shown in FIG. 1, and uses a combination of ultrasound tracking and optical tracking. The embodiment of the system 1 is particularly well suited to generate a natural range of motion profile for the shoulder joint. The natural range of motion profile may thus be for the movements of the arm relative to the scapula in a non-invasive natural state. The non-invasive natural state may be without disrupting a soft-tissue envelope covering the glenohumeral joint, prior to any dislocation, prior to any incisions in the soft tissue, all of which maneuvers could hamper any natural range of motion. The expression "native" range of motion could also be used, though the range of motion is the current range of motion of the patient, such as with pathologies, disorders and/or injuries. However, while the system 1 assists in this generating of a natural range of motion profile, other setups are possible, as will be described hereinafter.

The system 1 is configured for performing tracking of the humerus and/or the scapula, and tools, as described hereinafter, and concurrently referred to as objects for simplicity. The system 1 may have a controller 2. As shown, the controller 2 may be part of a computer, or may be implemented in the form of a personal computer, a laptop, a tablet, a server, etc., that may be dedicated to providing computer-assisted guidance and surgical flow assistance. The controller 2 may be configured for executing computer-readable program instructions suitable for the processing of datasets D related to tracking. The program instructions may originate from a medium either remote from the controller 2 or directly connected thereto. Among possible implementations, the program instructions may be stored on a non-transitory computer-readable medium which may be communicatively coupled to the controller 2.

As the system 1 performs a tracking operation to generate range of motion profiles, for example, the controller 2 may receive, generate and transfer at least some of the datasets D associated to the objects O, which may be of various types of information including spatial (e.g., position, orientation), surfacic and volumetric. The controller 2 may also be used to derive information from such datasets D, which may include modifying and/or combining some such datasets D. The controller 2 may be capable of parsing or otherwise registering any such dataset D so as to interpret it in terms of an object-agnostic coordinate system, which may be referred to as a reference coordinate system R, a frame of reference, a referential system, etc. It should be noted that the controller 2 may relate some of the datasets D to one another. For example, a first dataset $D_a$ and a second dataset $D_b$ may respectively represent the position and orientation of a humerus $O_a$ and of a scapula $O_b$ according to the common global referential system R. In some embodiments, a dataset, e.g., the first dataset $D_a$ may be interpreted in a first coordinate system and may be modified by registering it into another coordinate system such as the reference coordinate system R, for instance. In other words, the first and second datasets may be registered relative to one another in a common coordinate system, i.e., the reference coordinate system R. Thus, different arrangements are possible to track objects relative to one another. The tracking of the humerus relative to the scapula may be used to generate a range of motion profile indicative of the extent of movements possible in a shoulder joint, such as overhead range of motion, forward elevation, external rotation, abduction to external rotation, among others.

The system 1 of FIG. 1 provides, as an output, computer-assisted surgery guidance to the operator by timely communication (e.g., real-time, quasi real-time, though could be delayed as well) of the above datasets D and/or information, referred to henceforth as navigation data, in pre-operatively planning, peri-operatively, or during the surgical procedure, i.e., intra-operatively. In a particular embodiment, the system 1 is used pre-operatively, without disruptions to the soft tissue, though soft tissue disruptions are also possible. The system 1 may include various types of interfaces for the navigation data to be suitably communicated to the operator, for instance via the GUI 4 shown as part of the controller 2. In some embodiments, the tracked anatomical features can be displayed in real time on the GUI 4 during the computer-assisted surgery. The interfaces of the system 1 may be monitors, displays and/or screens including mounted devices, wireless portable devices (e.g., phones, tablets), head-up displays (HUD), augmented-reality devices such as the Hololens®, Microsoft® (Redmond, Washington), audio guidance devices and haptic feedback devices, mouse, keyboard, foot pedal, and any combination thereof, among many other possibilities. A single-device interface is also contemplated.

In terms of input, the system 1 may have access to some of the datasets D in the form of digital models for the various objects O, such as anatomical models including, but not limited to, bone model(s) (e.g., scapula, humerus), arm model(s), torso model(s) and model(s) of any other anatomical feature(s) of interest. Such anatomical models may consist in datasets containing information relating to surfacic and/or volumetric characteristics of corresponding anatomical features, such as a bone. This includes bone models that are for only a portion of a bone, or for a mix of resolutions for different parts of a bone, such as high resolution for the humeral head, and lesser resolution in the elbow area, in the case of shoulder surgery. The model could also include surfacic data for part of a bone, and an axis for a remainder of the bone. The anatomical models may be patient-specific, and may have been obtained pre-operatively or peri-operatively, using various imaging modalities. For example, the anatomical models may have been generated from magnetic resonance imagery, radiography in its various forms, ultrasound imaging, to name a few examples. As the case may be, a dataset corresponding to a bone model may be defined consistent with imaging conventions, e.g., with the X, Y and Z axes corresponding to the anterior, left lateral and cranial directions upon the patient lying supine. In some embodiments, the bone models may be obtained from a bone atlas or other suitable source based on factors such as gender, race, age, etc, for example as described in U.S. Pat. Nos. 8,884,618, and 10,130,478, the contents of both of which being incorporated herein by reference. In some such embodiments, the bone models may be digitally fitted to patient-specific data, such as, for instance, partial yet strategically selected data points, such as for joint surfaces of a bone, while a bone shaft may be taken from a bone atlas, for example. Such processing of the models may be carried out remotely or locally (e.g., via the controller 2). Likewise, storage of the bone models and/or models of any other anatomical features may be implemented remotely or locally (i.e., via a computer-readable memory).

Moreover, the system 1 may have an ultrasound imaging system 6 configured to generate some of the datasets D, though this is an option. The ultrasound imaging system 6 includes one or more ultrasound probe unit(s) 6*a* provided for producing signals indicative of characteristics pertaining to the objects O. The resulting signals may be communicated from an ultrasound imaging device 6*b* to the controller 2 to be processed into corresponding datasets D. Alternatively, the signals may be processed by device-specific processing units, such that the corresponding datasets D may be received by the controller 2 instead of the signals. The ultrasound imaging system 6 may be said to be modular as it can include a plurality of ultrasound probe unit(s) 6*a* and/or ultrasound imaging device(s) 6*b*.

Further, the CAS tracking system 1 may be configured such that the outputting of at least some of the navigation data from the controller 2 is timed with inputting of at least some of the datasets D into the controller 2. The CAS tracking system 1 may thus be said to provide the navigation data in real time or near real time, also known as live feed.

In accordance with some embodiments, a tracking system 8 is provided as part of the system 1. The tracking system 8 may include one or more tracking device(s) 8*a* including, for instance, a camera that tracks marker reference(s) 8*b*. The coordinate tracking system 8 can use either active or passive spatial references as markers of position and/or orientation. For example, as is known in the art, the tracking system 8 may optically see and recognize retroreflective devices as reference markers, so as to track objects, for example bones and tools, in six degrees of freedom (DOFs), namely in position and orientation along the X, Y and Z axes. Thus, the orientation and position of the limb in space can be determined using the information obtained from the spatial references, resulting in a corresponding dataset (for example, the dataset $D_b$) that is defined according to a corresponding coordinate system (for example the coordinate system R), which may in some cases be inherent to a reference marker or to the ultrasound probe unit 6*a* used therewith. The tracking system 8 may also include a dedicated computing device used to condition, digitize and/or otherwise process the signal produced by the camera. The tracking device 8*a* may be a 3D depth camera as a possibility (e.g., a Kinect™), that may not require passive spatial references as markers of position and/or orientation. Other 3D cameras can be used in other embodiments. For instance, the tracking device 8*a* may include conventional two-dimensional camera(s) (operated in mono- or stereo-vision configuration) operated with a shape recognition module which identifies, locates and processes two-dimensional identifiers (e.g., QR codes) as imaged in the two-dimensional images generated by the two-dimensional camera(s). In these embodiments, the shape recognition module can evaluate the distortion of the two-dimensional identifiers in the two-dimensional images (e.g., a square identifier becoming trapezoidal when bent) to retrieve three-dimensional model(s) of the two-dimensional identifiers and/or of the underlying anatomical feature.

In some embodiments, the ultrasound imaging system 6 is used to produce a signal indicative of at least one spatial and/or dimensional characteristic relating to biological tissue. According to conventional ultrasound-based detection principles, which are typical to conventional ultrasound probe units, an ultrasound emitter may be used to cast a sound wave and, upon an object being located within range of the ultrasound emitter, an echo of the sound wave is cast back to be sensed by an ultrasound sensor. In some embodiments, the ultrasound emitter and the ultrasound sensor may be separate from one another. However, in some other embodiments, the ultrasound emitter and the ultrasound sensor may be combined to one another in an ultrasound transducer performing both the ultrasound emission and the sensing functions. The echo may materialize upon the sound wave travelling through a first medium, such as skin, reaching a second medium of greater density compared to that of the first medium, such as a bone. As the speeds at which the sound waves may travel through various media depend on the respective physical properties of such media, characteristics of the echo (e.g., time elapsed between emission of the sound wave and the sensing of the echo, intensity of the echo relative to that of the sound wave, etc.) may be used to derive certain characteristics of the media through which the echo has travelled. In some embodiments, the functions of both the ultrasound emitter and the ultrasound sensor are performed by one or more ultrasound transducer transducers. In some embodiments, the ultrasound transducer may have one or more piezoelectric crystals emitting ultrasound signals based on corresponding electrical signals, and/or generating electrical signals based on received ultrasound signals. Any suitable type of ultrasound transducers can be used including, but not limited to, piezoelectric polymer-based ultrasound transducers such as poly(vinylidene fluoride)-based ultrasound transducers, capacitive ultrasound transducers, microelectromechanical systems (MEMS) based ultrasound transducers and the like.

Per the present disclosure, namely, in the exemplary case of orthopedic shoulder surgery, the ultrasound imaging system 6 may be configured to produce a signal indicative of a detailed spatial relationship between the ultrasound probe unit 6*a* and a bony articulation (which may be one being tracked by the tracking system 8), and also between constituents of the bony articulation such as soft tissue (e.g., skin, flesh, muscle, ligament) and bones. Resulting datasets may include measurements of a distance between contours associated to the bones, such as an epithelial contour associated to skin and a periosteal contour associated to the bones. The resulting datasets may also include measurements of thicknesses, surfaces, volumes, medium density and the like. Advantageously, updated signal production via the ultrasound imaging system 6 and ad hoc, quasi-real-time processing may produce datasets which take into account movement and/or deformation of one or more of the constituents of the limb. The ultrasound imaging system 6 may also include a dedicated computing device configured for conditioning and/or digitizing the signal.

In some implementations, the ultrasound imaging system 6 may be suitable for producing a signal indicative of surfacic, volumetric and even mechanical properties of the objects O to be tracked by the CAS tracking system 1. This may be achieved, for instance, by way of a multi-planar ultrasound system capable of operating simultaneously along multiple notional planes that are spaced and/or angled relative to one another, coupled to a suitably configured controller 2. Further, it is contemplated that other types of imaging systems, such as an optical coherence tomography (OCT) system, may be used in combination with the ultrasound imaging system 6. The type of additional imaging system may be selected, and combined with other type(s) as the case may be, to attain certain performance requirements in terms of effective range, effective depth, signal-to-noise ratio, signal acquisition frequency, contrast resolution and scale, spatial resolution, etc., among other possibilities. In some embodiments, partially exposed bone structures may be captured and/or referenced by the additional imaging system at any time before, during or after the surgery. Specifications of such imaging systems may thus be adapted, to some degree, based on requirements derived from typical characteristics of the objects O to be tracked.

As will be described in view of the above, a precise tracking of bone may be achieved using the system 1, regardless of certain materials, such as soft tissue, being overlaid thereon. Accordingly, a range of motion profile in a natural state of the patient can be acquired using ultrasound tracking with the system 1. Stated differently, a patient-specific range of motion, without soft tissue disruptions, can be obtained. This may be done preoperatively, and may be used in surgical planning. Moreover, since part of the imaging is done pre-operatively in a non-invasive manner, without skin perforations, sterility requirements may be loosened.

Figure 2:
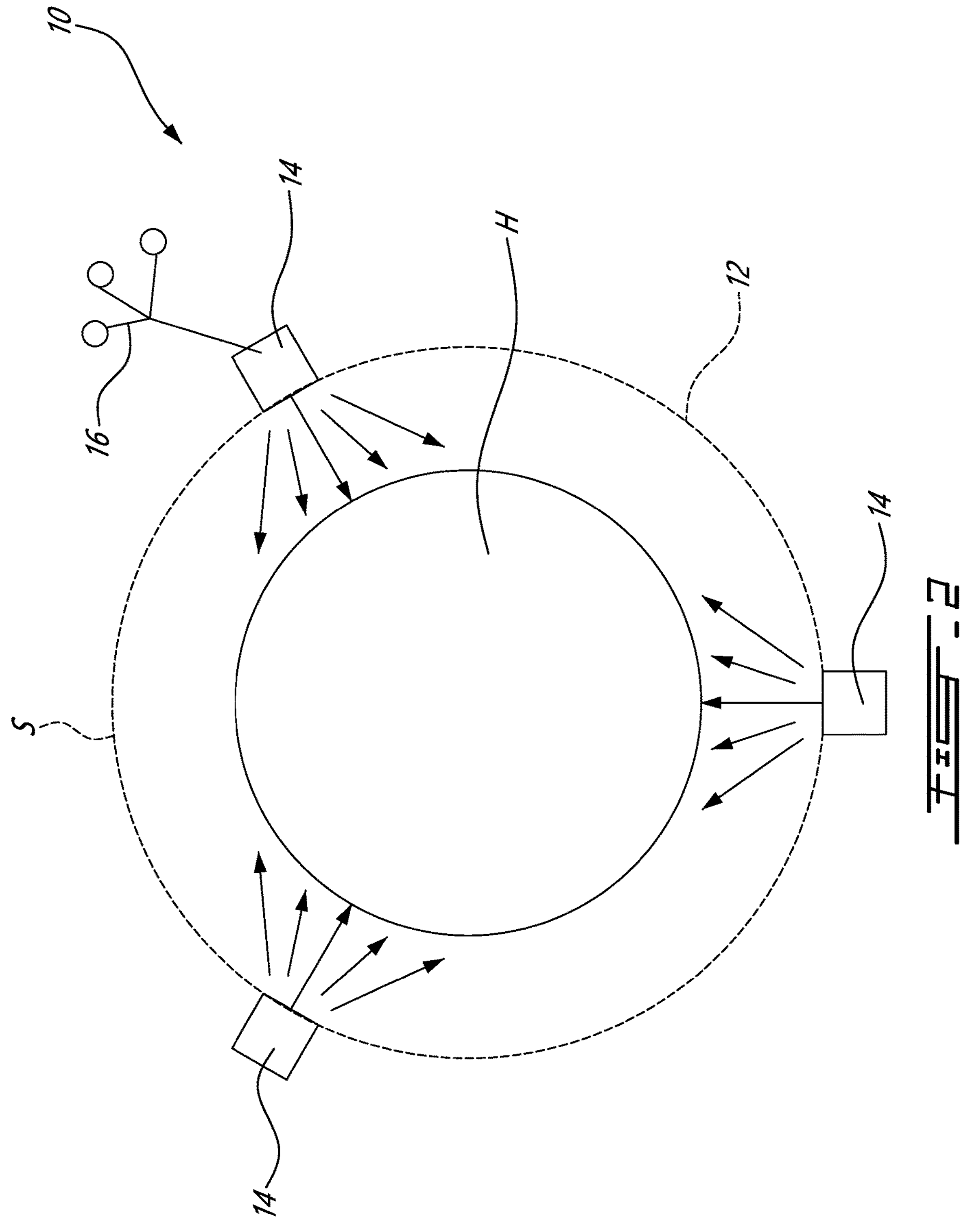
FIG. 2 is a schematic view of an ultrasound tracking device of a variant of the system of FIG. 1, used on the humerus.

The system 1, and specifically the tracking system 8, may be well suited to track ultrasound tracking devices 10 shown in FIG. 2. According to an embodiment, an ultrasound tracking device 10 is of the type that attaches to a body portion of a patient, and is used to track an axis or an anatomical feature of the body portion. For this purpose, the ultrasound tracking device 10 has a wearable holder 12, ultrasound probe units 14, and may have another trackable reference 16.

The wearable holder 12 is of the type that is mounted about the outer-skin surface S (a.k.a., exposed skin, epidermis, external soft tissue, etc.) of an anatomical feature, such as but not limited to the skin of the upper arm, covering the humerus H. The wearable holder 12 and the system using it, as will be described herein and as an example the ultrasound imaging system 6 of FIG. 1, may therefore be used to determine the position and/or orientation of the humerus. Accordingly, while portions of the bone may be exposed during surgery with the anatomical feature within the wearable holder 12, the bone will otherwise remain substantially subcutaneous. While the bone may be described herein as "underlying" the outer-skin surface S, it is to be understood that this does not exclude the possibility that certain portions of the bone may be at least partially exposed during surgery (e.g. by incisions, etc.) nor does this require or imply that the entirety of the bone must necessarily be unexposed and subcutaneous at all times, for instance in the case of laparoscopic procedures.

The ultrasound tracking device 10 including the wearable holder 12 is configured to be secured to the anatomical feature against which it is mounted in such a way that there is a no movement, or tolerable movement between the holder 12 and the anatomical feature. Algorithms can detect and compensate for movement using ultrasound processing combined with the optical tracking system. The position and the orientation of the holder 12 may also be trackable through space by the coordinate tracking device 8, whereby a tracking of the anatomical feature can be derived from a tracking of the ultrasound tracking device 10. The ultrasound tracking device 10 is therefore a non-invasive tool to be used to track the position and the orientation, and thus the movement, of the bone through space before, before, during or after the computer-assisted surgery, for instance relative to a global referential system.

The wearable holder 12 of the ultrasound tracking device 10 can take different forms to accomplish such functionality. In the depicted embodiment, the wearable holder 12 is in the form of a strap(s) that is mounted to the upper arm of the patient to be in fixed relative relationship with the humerus H. In an alternate embodiment, the wearable holder 12 is in the form a tight-fitting sleeve that is mounted to an anatomical feature of the patient to be in fixed relative relationship with the bone. The wearable holder 12 may essentially be a pressurized band around the limb to enhance contact. It is also considered to use a gel conforming pad to couple the holder 12 to the skin, as a possibility. Traditional coupling gel can also be used. In some embodiments, coupling gel of typical formulations as well as biocompatible gel (e.g., in vivo biocompatible or in vivo bioexcretable) can be used. The gel conforming pad may include acoustically transmissive material which can help the transmission of the ultrasound signals and returning echo signals thereacross. In another embodiment, the wearable holder is in the form of a vest to track the scapula, as described below. The wearable holder 12 may be annular and arranged to be at an axial location corresponding to a slice of the bone, to which the bone axis is normal, in a first scenario. However, it is also considered to have the holder 12 angled, in such a way that the bone axis is not normal to a plane passing though the holder 12. In doing so, the ultrasound tracking device 10 may produce a greater axial coverage of bone surface than for the first scenario. Other embodiments can also include independently placed sensors that are disposed in a non-planar but relevant scanning positions to obtain usable datasets.

Ultrasound probe units 14 are secured to the wearable holder 12. In an embodiment, the ultrasound probe units 14 include one or more transducers that emit an ultrasound wave and measure the time it takes for the wave to echo off of a hard surface (such as bone) and return to the face(s) of the transducer(s). In order to self-calibrate for the patient's individual speed of sound, some transducers are positioned accurately relative to others and as one emits waves, others listen and can compute the speed of sound based on well-known relative geometric positioning. Using the known speed of the ultrasound wave travelling through a bodily media, the time measurement is translated into a distance measurement between the ultrasound probe 14 and the bone located below the outer-skin surface S. The transducers in the probe units 14 may be single-element or multi-element transducers, or a combination of both. For example, the probe units 14 may have multiple elements arranged in a phased array, i.e., phased-array ultrasound probe units 14, having the capacity of performing multi-element wave generation for sound wave direction control and signal reconstruction. In some embodiments, the phased-array ultrasound probe unit 14 has a single ultrasound transducer operating in a phased-array arrangement. When sensors are not rigidly linked to others, the relative position can be found with self-location algorithms. Therefore, the probe units 14 used in the manner shown in FIG. 2 produce signals allowing local image reconstruction of the bone. The phased-array ultrasound probe units 14 are configured to emit ultrasound signals successively towards different portions of the anatomical features. In some embodiments, the ultrasound signals may be successively steered from one portion to another. Alternatively or additionally, the ultrasound signals may be successively focused on the different portions of the anatomical feature. In another embodiment, the ultrasound probe units 14 are ultrasound devices integrated into the ultrasound tracking device 10. The measurement is done by either triggering it manually, or automatically. In one embodiment, the measurement is repeated at regular intervals. The measurements are constantly being transferred to the ultrasound imaging device **6*b* of the system 1 (FIG. 1), for the position and orientation of the bone in space may be updated. In an embodiment, a reference marker 16 may be part of the ultrasound tracking device 10. These reference markers 16 may be active or passive, optical (including fiber optic Bragg grating), RF, electro-magnetic, inertial or even ultrasound. In the figures, optical reflective reference markers 16 are illustrated, in the form of three tokens or spheres, for illustrative purposes. The reference markers 16 are recognized by the position sensing system by their distinct geometries, such that a CAS tracking system such as the one described with reference to FIG. 1, can determine the position and orientation of the ultrasound tracking devices 10 in space using the reference markers. The tracking of the ultrasound tracking devices 10 in space, combined to the image reconstruction data from the ultrasound probe units 14, is used to track the anatomical features, such as the axis of the humerus H. For example, the image reconstruction from the signals of the ultrasound tracking device(s) 10 may be used in conjunction with the bone models obtained by the system 1 to match or register the reconstructed image from ultrasound with the 3D bone models in the system 1, and hence position and orient the bones in the 3D space, i.e., the coordinate system. The registration may be performed automatically by the system 1**.

The system 1 may thus be described as being an ultrasound tracking system for tracking a position and orientation of an anatomical feature(s) in computer-assisted surgery, such as the humerus and the scapula. The system 1 may include an ultrasound imaging system 6 having a phased-array ultrasound probe unit being adapted for emitting ultrasound signals successively towards different portions of the anatomical feature(s), measuring echo signals returning from said portions of said anatomical feature(s) and generating respective imaged echo datasets. A coordinate tracking system 8 may also be used to track coordinates of the ultrasound phased array probe unit during the measuring, and generating corresponding coordinate datasets. The controller 2 may be communicatively coupled to the ultrasound imaging system and the coordinate tracking system, the controller having a processor and a memory having stored thereon instructions that when executed by said processor perform the steps of: registering the imaged echo datasets in a common coordinate system based on the coordinate datasets; and tracking the position and orientation of the anatomical feature(s) based on the registering. The registering may include generating an anatomical feature model of the anatomical feature(s) based at least on the imaged echo datasets, and registering the anatomical feature model(s) in the coordinate system based on the coordinate datasets.

FIG. 2 is a cross-sectional view of the upper arm, with humerus H. The ultrasound probe units 14 are positioned around the bone on the outer-skin surface S via the wearable holder 12. The ultrasound probe units 14 are therefore distributed around the upper arm by the wearable holder 12. If the reference marker 16 is of the optical type, then the reference marker 16 must be in the line of sight of the position sensing system to be tracked. Other reference markers 16 may be used to increase a range of visibility of the ultrasound tracking device 10, and a depth camera could simply track the wearable holder. Again, it is contemplated to angle the wearable holder 12 relative to the upper arm to increase axial surface coverage and reconstruct a bone surface having a greater axial span.

A set of two or more ultrasound probe units 14 may be needed to determine the anatomical axis, as illustrated in FIG. 2. The wearable holder 12 surrounds the limb of the patient. The wearable holder 12 is positioned such that there are pairs of probe units 14 facing each other. The anatomical axis of the bone may be determined by locating the middle point between a pair of probe units 14 and forming a line from these points along the bone. Moreover, the readings from the probe units 14 may be used to perform a 3D image reconstruction of the bone, by the processor 2 of the system 1, and then identify a center of the bone segment, the anatomical axis passing through the center or being positioned relative to the center. The position of the wearable holder 12 in space may then be determined using the reference marker 16. Therefore, in an embodiment, one or more ultrasound probe units 14 are needed to determine the anatomical axis of a limb, if the reading from an ultrasound probe 14 provides a position from which more than one point on a line can be determined. It is also considered to position a pair of wearable holders 12 on a same bone, with an interconnection between them for example (or using the bone as being the "rigid connection" between the wearable holders 12). A single reference marker 16 could be shared in such a scenario, with the combination of the wearable holders 12 providing a further increase in axial surface coverage. In some embodiments, each wearable holder 12 may have a single ultrasound probe 14 equipped with an array of transducers operated in a phased array arrangement to determine the middle point, the cross-sectional shape, and/or an anatomical axis of the tracked bone.

Figure 3:
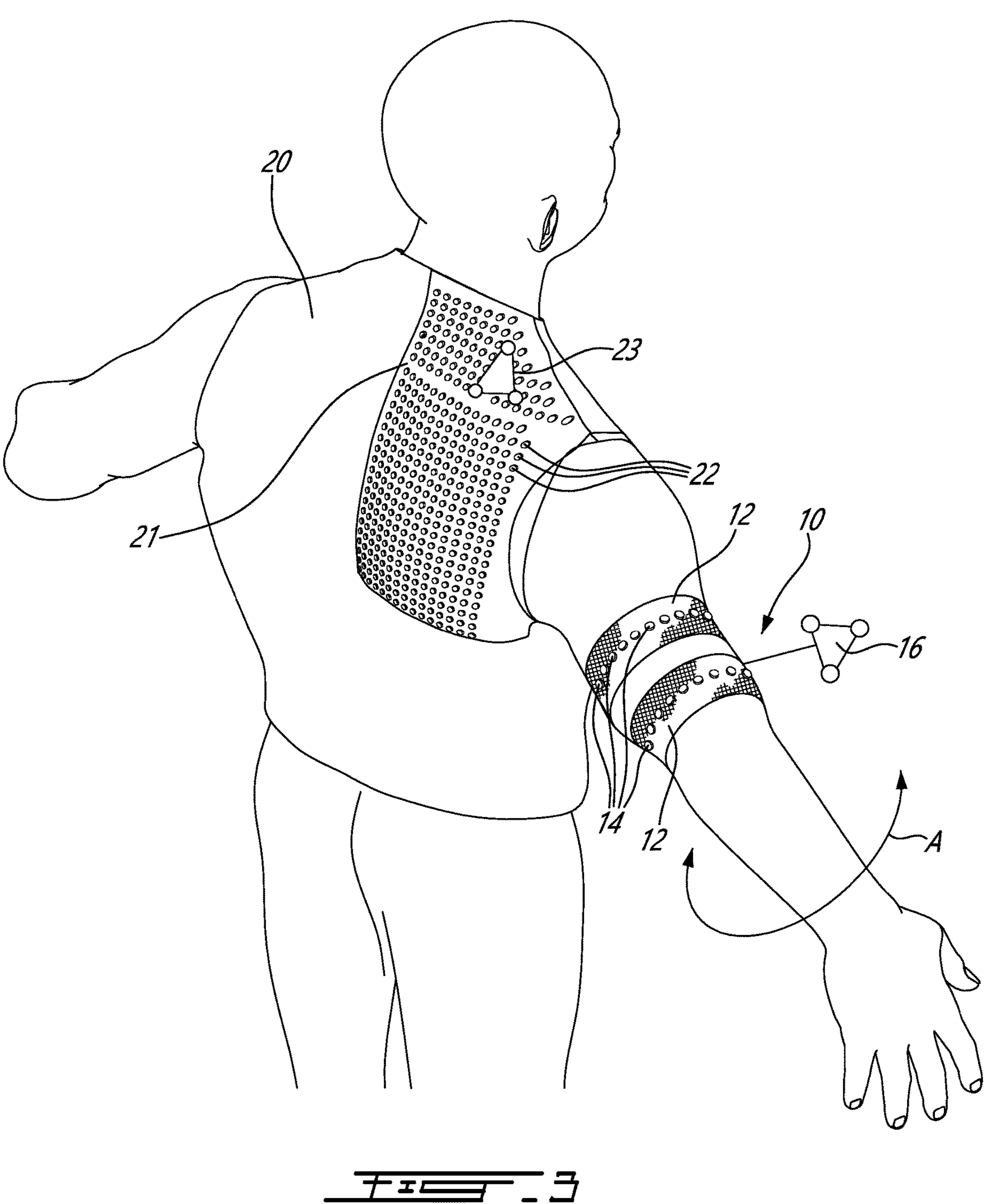
FIG. 3 is a schematic view of the ultrasound tracking device of FIG. 2 tracking the humerus and of a vest with ultrasound tracking, as part of a variant of the system of FIG. 1, used to track the scapula.

Referring to FIG. 3, another ultrasound tracking device operating in a similar fashion as the ultrasound tracking device 10 includes a vest 20 that is worn by the patient. The vest 20 may be made of a stretchable fabric that covers at least the upper torso of the patient, the vest 20 may be adapted to the patient, such as to the age, size, gender, etc. The vest 20 may therefore surround the scapula and may be used as a reference for the scapula. In a variant, an ultrasound imaging interface 21 covers at least a portion of the vest 20. As shown, the ultrasound imaging interface 21 is made of a solid acoustically transmissive material. In this specific embodiment, the ultrasound imaging interface 21 is provided in the form of a flexible mat covering the shoulder from the shoulder blade to the anterior portion of the pectoral muscles. The vest 20 may be tight enough to move with the torso of the wearer, so as to minimize any play. As shown, in this embodiment, ultrasound probe units 22 may be embedded in the flexible mat. The vest 20 may optionally further include a reference marker 23 to be tracked by the tracking device 8*a*, in the manner described above for the ultrasound tracking device 10.

Therefore, in the arrangement of FIG. 3, a wearer has the ultrasound tracking device 10 on his/her right arm, and a vest 20 covering the right shoulder. The wearer is in a normal condition, without any disruptions in the soft tissue. The wearer may therefore execute movements to delimit his/her range of motion, in a range of motion profile. The ranges of motion can be said to be in a natural state, in that the wearer has not suffered any cuts or alterations to his/her soft tissue. The wearer can thus move relatively freely, without the ultrasound tracking device 10 and/or the vest 20 being substantial encumbrances. However, this is optional, as it is possible to secure tracker devices on the bones.

With the system 1 operational, movements may thus be performed to create a natural range of motion profile with the wearer equipped with the ultrasound tracking device 10 and/or the vest 20. The movements may thus be tracked and recorded by the system 1, in order to generate a range of motion profile. The range of motion profile may include one or more of overhead range of motion, forward elevation, external rotation, abduction to external rotation, among others. The movements are generally depicted by arrow A in FIG. 3. The range of motion may also include a location of a center of rotation of the glenohumeral joint.

While the system 1 may enable such creation using the ultrasound imaging system 6 and the coordinate tracking system 8, other tracking modalities are considered. For example, inertial sensors could be used to track relative orientation of the humerus relative to the scapula, with or without optical tracking to track a position and orientation of the inertial sensors. The inertial sensors could be combined on-skin palpation to assist in registering the bones in the tracking. This is an example among others.

Figure 4:
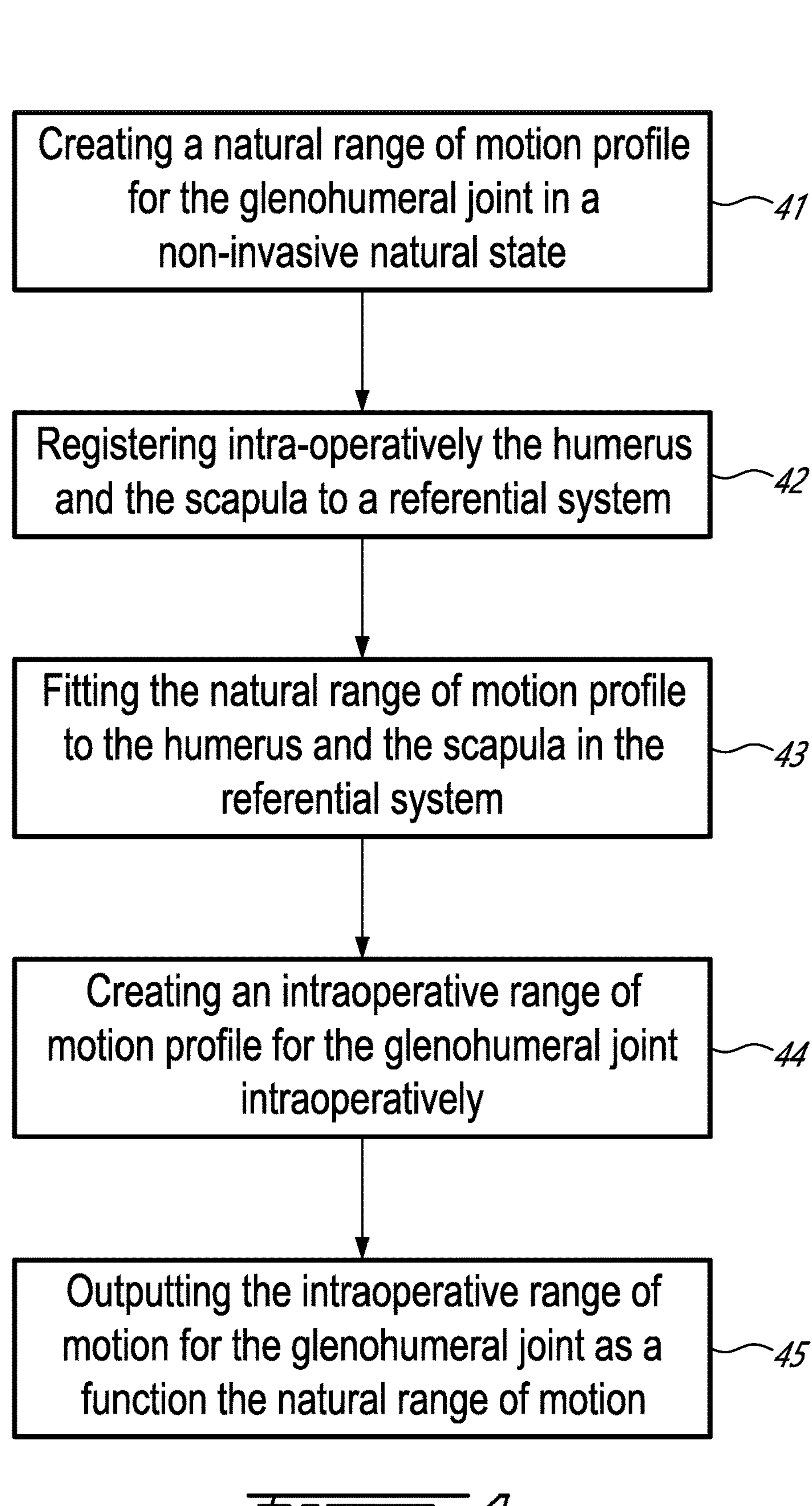
FIG. 4 is a flow chart of a method for computer-assisted guidance in glenohumeral joint surgery in accordance with a variant of the present disclosure.

Therefore, referring to FIG. 4, there is illustrated a method 40 for computer-assisted guidance in glenohumeral joint surgery. The glenohumeral joint surgery may be of different types, such as total shoulder arthroplasty, total reverse shoulder arthroplasty, partial shoulder arthroplasty, or other orthopedic shoulder surgeries that include alterations to the humerus and/or scapula, etc, and may even be used in some shoulder surgical procedures that attend to tissue in the shoulder (e.g., tendons, ligaments, cartilage, osteophytes). The method 40 may be performed for instance by the system 1 of FIG. 1, or by any other appropriate computer-assisted surgery system that may have a processor unit, and a non-transitory computer-readable memory communicatively coupled to the processor and comprising computer-readable program instructions executable by the processor unit.

According to step 41, a natural range of motion profile may be created for the glenohumeral joint by tracking movement of the humerus relative to the scapula of the glenohumeral joint in a non-invasive natural state. Step 41 may include tracking the movement pre-operatively without disrupting a soft-tissue envelope covering the glenohumeral joint, though it is also possible to attach trackers directly to the bones, including on the humerus. In a variant, the patient is still such that the scapula does not move. Step 41 may also be performed peri-operatively or intra-operatively. The natural range of motion profile may include values pertaining to overhead range of motion, forward elevation, external rotation, and/or abduction to external rotation. The natural range of motion profile may also include a location of a center of rotation of the glenohumeral joint.

The glenohumeral joint may then be exposed, by incisions to the soft tissue (though it could have been exposed before). This may be done manually, by surgical robot, etc. This may occur in the peri-operative phase or in the intra-operative phase of surgery. In a variant, a time delay occurs between step 41 and subsequent steps of the method 40, which time delay may be in the magnitude of minutes, hours, weeks, etc.

In an embodiment, tracking movement of the humerus relative to the scapula of the glenohumeral joint in the non-invasive natural state may include tracking the humerus and the scapula using an ultrasound imaging device(s) and optionally optically tracking the ultrasound imaging device(s), such as those described in FIGS. 1, 2 and 3.

Step 41 in the method 40 may also be more generally include a step of obtaining the natural range of motion profile for the glenohumeral joint. For example, the natural range of motion profile may be created by or with a first CAS system, and the rest of the steps of the method 40 may be performed by or with a second CAS system. In such a scenario, and in other scenarios, the obtaining of the natural range of motion profile may include creating it or acquiring the natural range of motion profile as created by another CAS system.

According to step 42, the humerus and/or the scapula are registered intra-operatively to a referential system. In a variant, this may be done using a registration pointer that is tracked by an optical tracking system, such as the coordinate tracking system 8 of the system of FIG. 1. In a variant, the registration may be done with optical tools such as a depth camera, and/or by using or by connecting inertial sensors to the bones. Image processing may be done from a live camera feed to recognize and optionally generate 3D surfaces of the bones, to be used in the registration. The registration may include obtaining points on the surfaces of the bones to generate three-dimensional models of surfaces of the bones. The registration may further include merging existing virtual bone models to the three-dimensional models of surfaces of the bones, the existing bone models being obtained via other imaging modalities (e.g., radiography, MRI, etc) or through an atlas of non-patient specific bone models, as explained above. The registration may further including tracking and outputting live tracking data for the humerus and/or scapula, in the referential system. For example, the tracking may include outputting data pertaining to a relative orientation of the humerus relative to the scapula. The outputting data may optionally take the form of a live display of bone models on a user interface, with live updates of the relative position and orientation of the bones. The display of the bone models may be in one or more two-dimensional graphic images and/or in three-dimensional graphic images, for instance in addition to the numeric data pertaining to the position and orientation of the bones.

From the registering of the bones in step 42, the bones may be tracked continuously relative to the referential system, as desired by an operator. The continuous tracking may include interruptions, for example when the CAS system is in standby, or during surgical workflow steps in which live bone tracking is not required. The tracking of the bones may be performed during subsequent steps of the method 40, with the tracking used notably in step 44 described below.

According to step 43, the natural range of motion profile is fitted to the humerus and the scapula in the referential system. Accordingly, for subsequent tracking of movements of the humerus relative to the scapula, the movements may have data associating current movements to the natural range of motion profile. More particularly, fitting may entail merging the natural range of motion profile with the humerus and scapula in the referential system, now that the humerus and scapula are tracked in the referential system, subsequent to step 42. This may mean that the CAS system knows the extent of movement of the humerus relative to the scapula in the referential system, in the natural range of motion of the scapula.

Further surgical steps may occur in parallel to step 43 or after step 43, while tracking may or may not be done simultaneously/concurrently. For example, dislocation, resection of the bones, alterations, resurfacing, etc, may be executed. Such steps may include the installation of implants and/or of provisional implants. As the humerus and/or the scapula are altered from their natural state (e.g., native state), the surgical steps may have an impact on the behavior of the glenohumeral joint. For example, the surgical steps may result in a variation in soft tissue laxity in comparison to the natural state. Likewise, the range of motion of the glenohumeral joint may be affected by the surgical steps.

In a variant, the surgical steps include the surgeon's bone manipulations for the placement of the glenohumeral joint implants or implant provisionals (e.g., glenosphere or glenoid sphere, humeral tray, humeral head, glenoid tray, etc). Various types of sensors may also be used, for instance in the case of provisionals (also known as trial implants), in order to quantify joint laxity. The force data may be provided to the system 1 or like CAS providing guidance in the surgical procedure. In a variant, a surgical robot may be used in positioning the humerus relative to the scapula, and the robotic arm may provide force measurements as a function of the relative position.

In shoulder surgery, such as reverse shoulder surgery, a plane of resection on the humeral head is typically oriented to a desired retroversion and/or inclination. These angle values may be relative to an anatomical axis of the humerus that extends along the length of the humerus. Retroversion, a.k.a., retroversion angle, may be defined as being the angle between a projection of a normal of the resection plane onto a transverse plane of the humerus, relative to a medio-lateral axis. Inclination, a.k.a., inclination angle, may be defined as the angle between a projection of a normal of the resection plane onto the frontal plane of the humerus, relative to the anatomical axis of the humerus. Other or different angles may also come into consideration when planning and performing a cut on the humeral head. The system 1 may track these angles during surgery, and the method 40 may include tracking and outputting data associated with alterations to the humerus and/or scapula. This may occur before resection, during resection, and after resection.

According to step 44, an intraoperative range of motion profile for the glenohumeral is created by tracking movement of the humerus relative to the scapula of the glenohumeral joint intraoperatively. This implies that alterations have been made to the humerus and/or scapula, and/or to bodily tissue in the glenohumeral joint. In a variant, the tracking of the movements uses sensors on the bones that have been described for step 42, such as optical reference markers **8*b***, inertial sensors, for example. The tracking of the movements may rely on a depth camera to track movements of the bone in the creation of the intraoperative range of motion. The movements may be induced by operating room personnel, by a surgical robot that can optionally simultaneously measure forces to assist in delimiting the ends of the range of motion.

According to step 45, the intraoperative range of motion for the glenohumeral joint is output as a function of the natural range of motion. The intraoperative range of motion may be expressed in relative values that may indicate a gain or loss of range of motion, such as in %, relative to the natural range of motion. The intraoperative range of motion can also or instead by expressed in absolute values, such as in degrees or distances.

In an embodiment, the intraoperative range of motion may not be suitable in that the values may be below expectations, or in regression relative to the natural range of motion. Accordingly, additional surgical steps, as described above as performed in parallel to or after step 43, may be required to enable a new position and/or orientation of the glenohumeral joint. This may include modifying provisionals, changing liners, selecting a different implant thickness, etc. Steps 44 and 45 may then be repeated in order to update the intraoperative range of motion.

If the operator is satisfied with the values of intraoperative range of motion and soft tissue balancing, additional surgical steps may be performed to finalize surgery. For example, the implants may be placed, and the surgical site may be closed, the cut may be covered.

Figure 5:
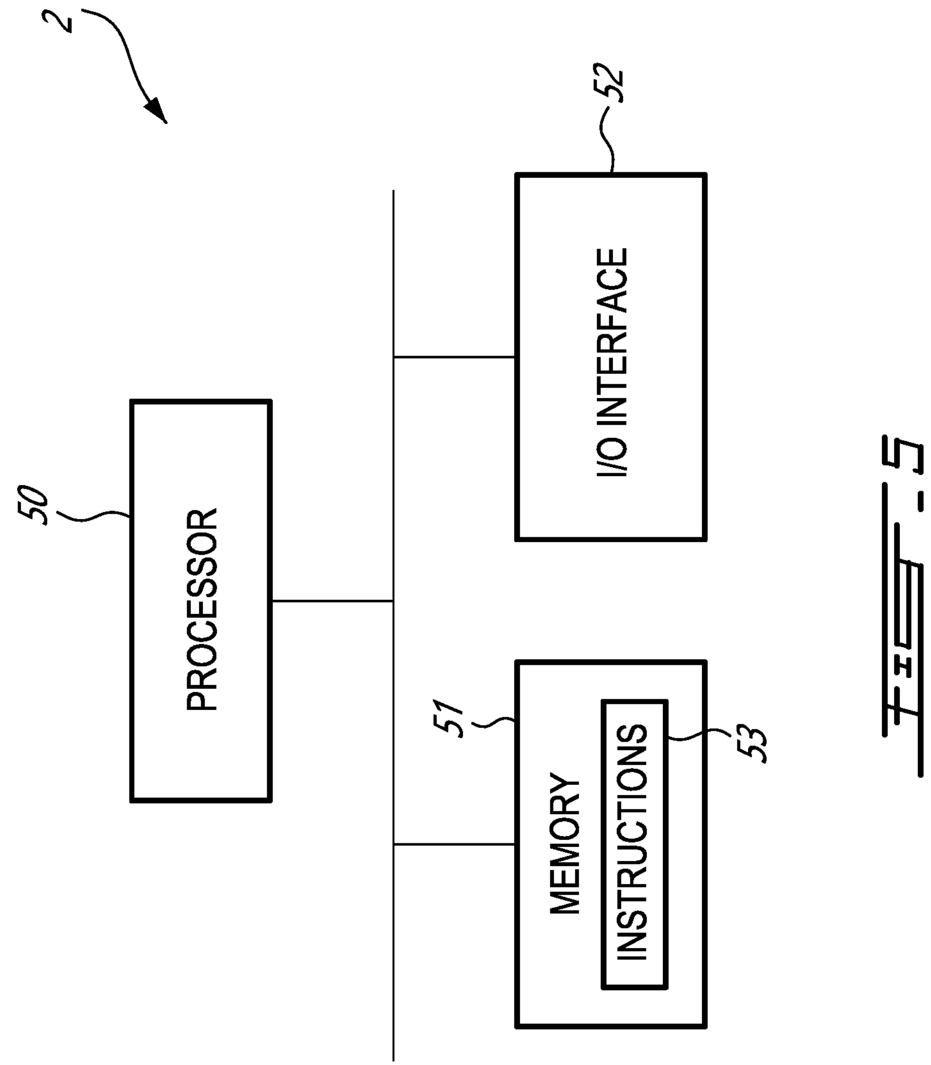
FIG. 5 is a schematic view of an example of a computer of the system of FIG. 1, in accordance with one or more embodiments.

Referring to FIG. 5, in a variant, the method 40 may be computer-readable program instructions executable by the processor unit and stored in a non-transitory computer-readable memory communicatively coupled to the processor of the computer 2 of the system 1.

The computer 2 can have a processor 50, a memory 51, and I/O interface 52. Instructions 53 for tracking a position and an orientation of an anatomical feature during computer-assisted surgery can be stored on the memory 51 and accessible by the processor 50.

The processor 50 can be, for example, a general-purpose microprocessor or microcontroller, a digital signal processing (DSP) processor, an integrated circuit, a field-programmable gate array (FPGA), a reconfigurable processor, a programmable read-only memory (PROM), a system on a chip, an embedded controller, or any combination thereof.

The memory 51 can include a suitable combination of any type of computer-readable memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like.

Each I/O interface 52 enables the computing device 2 to interconnect with one or more input devices, such as the ultrasound imaging system or its ultrasound probe unit(s), the coordinate tracking system, keyboard(s), mouse(s), or with one or more output devices such as display screen(s), computer memory(ies), network(s) and like.

Each I/O interface 52 enables the system 1 to communicate with other components, to exchange data with other components, to access and connect to network resources, to server applications, and perform other computing applications by connecting to a network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX, Zigbee), SS7 signaling network, fixed line, local area network, wide area network, and others, including any combination of these.

It is intended that the instructions 53 may be executed to receive the imaged echo dataset(s), receive the coordinate dataset(s), to register the received imaged echo datasets in the common coordinate system X, Y, Z and to track the position and orientation of the anatomical feature. In some embodiments, a software application to execute the instructions 53 is stored on the memory 51 and accessible by the processor 50 of the computing device 2. In some embodiments, the software application can be locally or remotely stored. The computing device 2 and the instructions to be executed described above are meant to be examples only.

Accordingly, the system 1 and/or the method 40 enable evaluating the shoulder laxity and range of motion using navigation tools, but without disrupting the soft tissue envelope of the joint, in pre-operative steps. The system 1 and the method 40 may use trackers in a manner that avoids dislocating the joint, and conducting a range of motion assessment before the soft tissues are disrupted by the dislocation. However, the system 1 and/or the method 40 may be used to conduct the range of motion assessment before the skin is compromised by the incision, to provide data associated to the natural state of the shoulder joint.

The invention claimed is:

1. A system for computer-assisted guidance in glenohumeral joint surgery comprising:

a processor unit, and a non-transitory computer-readable memory communicatively coupled to the processor and comprising computer-readable program instructions executable by the processor unit for:

obtaining a natural range of motion profile for the glenohumeral joint by tracking movement of a humerus relative to a scapula of the glenohumeral joint in a non-invasive natural state, registering intra-operatively the humerus and the scapula to a referential system, intra-operatively fitting the natural range of motion profile to the humerus and the scapula in the referential system, creating an intraoperative range of motion profile for the glenohumeral joint by tracking movement of the humerus relative to the scapula of the glenohumeral joint intraoperatively in the referential system, and outputting the intraoperative range of motion for the glenohumeral joint as a function of the natural range of motion, the intraoperative range of motion for the glenohumeral joint as a function of the natural range of motion being expressed in a percentage and/or in degrees.

2. The system according to claim 1, wherein obtaining the natural range of motion profile includes creating the natural range of motion profile for the glenohumeral joint.

3. The system according to claim 2, wherein creating the natural range of motion profile for the glenohumeral joint includes tracking movement of the humerus relative to the scapula of the glenohumeral joint in the non-invasive natural state.

4. The system according to claim 3, wherein tracking movement of the humerus relative to the scapula of the glenohumeral joint in the non-invasive natural state includes tracking the movement pre-operatively without disrupting a soft-tissue envelope covering the glenohumeral joint.

5. The system according to claim 3, wherein tracking movement of the humerus relative to the scapula of the glenohumeral joint in the non-invasive natural state includes tracking the humerus and the scapula using at least one ultrasound imaging device.

6. The system according to claim 5, wherein tracking the humerus relative to the scapula using at least one ultrasound imaging device includes tracking the scapula with a vest on soft-tissue covering the scapula, the vest including a plurality of ultrasound probe units.

7. The system according to claim 6, including the vest with the plurality of ultrasound probe units.

8. The system according to claim 6, wherein tracking movement of the scapula includes optically tracking the vest.

9. The system according to claim 5, wherein tracking the humerus relative to the scapula using at least one ultrasound imaging device includes tracking the humerus with a wearable band on soft-tissue covering the humerus, the wearable band including a plurality of ultrasound probe units.

10. The system according to claim 9, including the wearable band with the plurality of ultrasound probe units.

11. The system according to claim 9, wherein tracking movement of the humerus relative to the scapula includes optically tracking the wearable band.

12. The system according to claim 2, wherein creating the natural range of motion profile for the glenohumeral joint includes creating the natural range of motion profile pre-operatively or peri-operatively, prior to soft-tissue incisions being made to access the glenohumeral joint.

13. The system according to claim 1, wherein registering intra-operatively the humerus and the scapula to a referential system includes obtaining points on the humerus and on the scapula.

14. The system according to claim 13, wherein registering intra-operatively the humerus and the scapula to a referential system includes merging virtual bone models to the points obtained on the humerus and on the scapula.

15. The system according to claim 14, wherein merging virtual bone models includes obtaining bone models from an atlas.

16. The system according to claim 1, further including tracking the humerus and the scapula relative to the referential system continuously after the registering.

17. The system according to claim 16, wherein tracking the humerus and the scapula includes tracking alterations to the humerus.

18. The system according to claim 16, wherein tracking alterations to the humerus includes a retroversion angle and/or an inclination angle for a plane of resection.

19. The system according to claim 1, wherein outputting the intraoperative range of motion includes outputting a gain or loss of range of motion relative to the natural range of motion.

20. A system for computer-assisted guidance in glenohumeral joint surgery comprising:

a processor unit, and a non-transitory computer-readable memory communicatively coupled to the processor and comprising computer-readable program instructions executable by the processor unit for:

obtaining a natural range of motion profile for the glenohumeral joint by tracking movement of a humerus relative to a scapula of the glenohumeral joint in a non-invasive natural state;

in an intra-operative phase of the glenohumeral joint surgery:

registering intra-operatively the humerus and the scapula to a referential system for tracking of the humerus and the scapula relative to the referential system, fitting the natural range of motion profile to the humerus and the scapula in the referential system, and creating an intraoperative range of motion profile for the glenohumeral joint by tracking movement of the humerus relative to the scapula of the glenohumeral joint in the referential system; and outputting the intraoperative range of motion for the glenohumeral joint as a function of the natural range of motion, the intraoperative range of motion for the glenohumeral joint as a function of the natural range of motion being expressed in a percentage and/or in degrees.

* * * * *